United States Patent [19]
Nakaichi et al.

[11] Patent Number: 6,004,263
[45] Date of Patent: Dec. 21, 1999

[54] ENDOSCOPE WITH DETACHABLE OPERATION UNIT AND INSERTION UNIT

[75] Inventors: Katsumi Nakaichi; Shinji Yamamori; Hironori Kuroyone; Norio Ishikawa; Kohei Ono; Hidehiro Hosaka, all of Tokyo, Japan

[73] Assignee: Hihon Kohden Corporation, Tokyo, Japan

[21] Appl. No.: 08/815,928

[22] Filed: Mar. 13, 1997

[30] Foreign Application Priority Data

Mar. 13, 1996 [JP] Japan .................................. 8-056095
Mar. 13, 1996 [JP] Japan .................................. 8-056096

[51] Int. Cl.$^6$ ...................................................... A61B 1/01
[52] U.S. Cl. ........................ 600/176; 600/146; 600/136; 600/131; 600/179; 600/120
[58] Field of Search .................................... 600/136, 139, 600/131, 146, 147, 148, 149, 150, 169, 182, 176, 120

[56] References Cited

U.S. PATENT DOCUMENTS

| | | |
|---|---|---|
| 4,534,339 | 8/1985 | Collins et al. . |
| 4,624,243 | 11/1986 | Lowry et al. . |
| 4,748,969 | 6/1988 | Wardle . |
| 4,790,295 | 12/1988 | Tashiro .............................. 600/182 X |
| 4,911,148 | 3/1990 | Sosnowski et al. .................... 600/136 |
| 5,168,864 | 12/1992 | Shockey ............................. 600/146 X |
| 5,518,502 | 5/1996 | Kaplan et al. ...................... 600/169 X |

*Primary Examiner*—John P. Leubecker
*Attorney, Agent, or Firm*—Sughrue, Mion, Zinn, Macpeak & Seas, PLLC

[57] ABSTRACT

An eyepiece optical system, an illuminating lamp, and a battery 2 are housed in an operation unit 2. An insertion unit in which an image transmitting optical fiber bundle and an illumination light transmitting optical fiber bundle are incorporated is detachably coupled with the operation unit through a coupling unit. The insertion unit is bent using a bending wire attached to the distal end thereof and coupled to the operation unit by a wire operating mechanism. An anti-clouding material can be disposed on a surface of the distal end of the insertion unit to protect it against clouding.

11 Claims, 11 Drawing Sheets

ENDOSCOPE WITH DETACHABLE OPERATION UNIT AND INSERTION UNIT

BACKGROUND OF THE INVENTION

1. Field of the Invention

The invention relates to an endoscope for optically observing the body cavity of the patient, and particularly to an endoscope for inserting an endotracheal tube which enables an endotracheal tube to be inserted safely, surely, and rapidly into the trachea of a patient whose airway must be urgently opened because of an injury due to an accident or a disaster, a sudden attack of a disease, or the like. Further, the invention relates to an endoscope which is inserted into a living body and used for optically observing the body cavity, and particularly to an endoscope having a distal end structure which can be produced economically and easily.

2. Related art

Conventionally, when an endotracheal tube is to be inserted into the trachea of a patient, the oral cavity 51 of the patient is forcedly opened by using a laryngoscope 52 as shown in FIG. 11, and the endotracheal tube 53 is then inserted while observing an inner portion of the throat. In some cases, however, the portion through which the endotracheal tube 53 is to be inserted cannot be visually checked because the laryngoscope 52 is hard and used only for opening the mouth and illuminating an inner portion of the throat. In the case of the oral intubation, an endotracheal tube is usually inserted while directly observing the glottis in the oral cavity. In a usual posture, however, it is anatomically impossible to directly see the glottis. As shown in FIG. 11, therefore, the head is backwardly tilted, and the root of the tongue is pressed by a blade of the laryngoscope 52 thereby allowing the glottis to be directly observed.

In the case of deformation or a trauma on the face due to an accident or a disaster, microstomia, a tumor or a damage of the lips, or the like, however, it is difficult to open the mouse mouth. In the case of a phyma in the oral cavity or of the throat, teeth abnormality, a trauma on the face, or the like, moreover, it is difficult to insert the blade of the laryngoscope itself. In the case where the patient suffers from brevicollis or is corpulent or the cervical vertebra is inflamed or damaged, it is difficult to backwardly tilt the head. In the case of cleft palate, maxillary and mandibular micrognathism, macroglossia, or maxilla abnormality, it is difficult to exclude the tongue and press the root of the tongue by using the blade of the larygoscope.

In such cases, the endotracheal tube is barely inserted into the trachea. Conventionally, therefore, the blade of the laryngoscope is replaced with another one in accordance with the each case, or in some cases intubation is blindly attempted on the basis of feel only. Therefore, there arises a problem in that the endotracheal tube cannot be safely, surely, and rapidly inserted into the trachea.

As a method which can solve the problem, a method is known in which an insertion unit of an endoscope is passed through the inner space of an endotracheal tube and the endotracheal tube is inserted into the trachea while visually observing the body cavity of a patient by means of the endoscope. According to this method, the pharynx, the larynx, the trachea, and the like can be visually checked, and hence the endotracheal tube can be inserted safely, surely, and rapidly into the trachea.

In the endoscope device of the prior art, a so-called endoscope which is to be inserted into the human body and used for observing the body cavity, and a light source which emits illumination light for illuminating the body cavity are separately configured, and connected to each other through a light conductor cable so that the body cavity is illuminated, thereby enabling an image of the body cavity to be observed. The light source can operate when it is connected to an external power source.

On the other hand, in an endoscope, is illumination light transmitting optical fiber bundle and an image transmitting optical fiber bundle are passed through a slender resin tube. Such an endoscope is used for optically observing the body cavity of a living body while inserting the resin tube into the body cavity through the oral cavity or the nasal cavity. In the endoscope of the prior art, a pedestal made of a metal or the like is attached to the distal end of the resin tube, holes through which the distal ends of the illumination light transmitting optical fiber bundle and the image transmitting optical fiber bundle are passed are formed in the pedestal, and the distal ends of the fiber bundles are attached to the holes and fixed by adhesion or another method. As a structure for bending the resin tube, a structure is usually employed in which the distal end of a wire rope configured by metal thin wires is fixed to the pedestal by soldering or the like, the wire rope is pulled out to the outside through the resin tube, and the resin tube is bent by producing or relaxing tension in the wire rope.

In the thus configured endoscope device of the prior art, the endoscope, the light source, and the power source which are separately configured must be independently prepared. When such an endoscope device is to be used in a confused situation such as an accident or disaster location, therefore, these components cannot be easily prepared. In such a location, furthermore, it is difficult to ensure a power source.

When the endoscope is connected to the light source through the light conductor cable, various problems are produced. Namely, the light source cannot be placed at a position where the endoscope can use the light source, because of the restriction imposed by the light conductor cable; the fiber may hinder medical aid work so as to make it difficult to do; the light conductor cable may be erroneously pulled during medical aid work, with the result that the light source falls; or, if the light conductor cable is accidentally pulled when the endoscope is inserted into the human body, the patient may be damaged.

In such a confused location, furthermore, it is difficult to find a safe place where the endoscope can be placed after its use, and the endoscope is often placed on the ground. In this case, there is a fear that the endoscope is stamped and becomes broken under a situation where persons move around for medical aid. Particularly, the insertion unit of the endoscope is brittle. When the insertion unit is stamped once, therefore, it is inevitably broken. When the insertion unit is broken, the whole of the endoscope including the operation unit must be replaced with a normal one, with the result that the damage is further increased.

When many persons are injured, there may occur a case where an endoscope which has been used for an injured person must be used as it is for another injured person. In this case, there arises a problem in that, if an injured person carries any germ, other injured persons may be infected. In order to prevent infection, the endoscope must be sterilized. However, sterilization of an endoscope of the prior art requires much effort and a long time, thereby producing another problem in that such an endoscope cannot cope with an emergency.

In the thus configured endoscope of the prior art, a number of holes must be formed in the pedestal made of a metal or the like by machining or another method, and then the distal ends of the fiber bundles must be inserted into the holes and then fixed. This produces a problem in that the working and assembling steps require a long time and the resulting endoscope is expensive. Since a number of holes are formed in the pedestal of a small diameter, the thickness between holes is small. This causes a fear that the pedestal may be broken.

When the pedestal is omitted in order to simplify the structure, the fiber bundles cannot be firmly fixed, thereby causing another problem in that the performance of the endoscope cannot be sufficiently ensured. Particularly, such a structure has a disadvantage that the wire may meander and fail to satisfactorily conduct the bending operation. When a wire guide is formed in the resin tube in order to prevent the wire from meandering, the structure is complicated and the endoscope becomes expensive.

SUMMARY OF THE INVENTION

The invention has been conducted in view of the above-mentioned circumstances. It is an object of the invention to provide an endoscope for inserting an endotracheal tube which, even when a person is injured due to an accident or a disaster or suddenly attacked with a disease, enables an endotracheal tube to be inserted safely, surely, and rapidly into the trachea of the patient, and which, even when the insertion unit of the endoscope is broken or contaminated, can suppress the damage lower and easily cope with the damage.

Another object of the invention is to provide an economical endoscope which has a distal end structure that is simple in structure and low in cost, and which can be easily assembled without impairing the performance.

In order to attain the object, the endoscope for inserting an endotracheal tube of the present invention is provided in that the endoscope comprises: a tubular insertion unit which is to be inserted into a trachea of a living body through an endotracheal tube, the insertion unit having a connecting portion and bendable portion and incorporating at least: an illumination light transmitting optical fiber bundle which guides an illumination light to a distal end; an image transmitting optical fiber bundle through which an image of an object illuminated with the illumination light is transmitted to the connecting surface of the insertion unit; and a wire for bending the bendable portion; an operation unit having at least: a light source which illuminates the illumination light transmitting optical fiber bundle to produce the illumination light; a power source which supplies a power to the light source; an eyepiece for observing the image of the object which is guided through the image transmitting optical fiber bundle; and a wire operating mechanism which produces and relaxes tension in the wire; and a coupling unit which detachably couples the insertion unit with the operation unit.

The endoscope for inserting an endotracheal tube of the present invention is provided in that a proximal end portion of at least the image transmitting optical fiber bundle of the insertion unit, and the eyepiece of the operation unit are coaxially disposed, the proximal end portion being on the side of the operation unit.

The endoscope for inserting an endotracheal tube of the present invention is provided in that the coupling unit has a pressing member which causes a proximal end portion of at least the image transmitting optical fiber bundle of the insertion unit to be coupled under a condition where the proximal end portion is pressed toward the eyepiece of the operation unit, the proximal end portion being on the side of the operation unit.

In order to attain the object, the present invention is an endoscope comprising an insertion unit which is to be inserted into a living body, and which has a bendable portion and a resin tube, the resin tube incorporating at least: an illumination light transmitting optical fiber bundle which guides illumination light to a distal end; an image transmitting optical fiber bundle through which an image of an object illuminated with the illumination light is transmitted to the connecting surface of the insertion unit; and a wire for bending the bendable portion, and characterized in at least one of a distal end of the illumination light transmission fiber, a distal end of the image transmitting optical fiber bundle, or a distal end of the wire is integrally bonded together by a resin at a distal end of the insertion unit.

The endoscope of the present invention is provided in that the resin tube is a multi-lumen tube having: at least a larger inner space through which the illumination light transmitting optical fiber bundle and the image transmitting optical fiber bundle are passed; and a smaller inner space through which the wire is passed.

The endoscope of the present invention is provided in that the surface of the distal end of the insertion unit is protected against clouding. For example, the surface of the distal end of the insertion unit is coated with anti-clouding material. The other example is that an anti-clouding membrane which is integrally molded with the resin is disposed at the distal end of the insertion unit.

The endoscope of the present invention is provided in that the distal end of the image transmitting optical fiber bundle is integrally bonded by a resin at the distal end of the insertion unit through a pipe in which a lens is integrally concentrically molded by a resin.

The endoscope of the present invention is provided in that the wire is made of a resin.

In the endoscope of the present invention, the light source and the power source are incorporated in the operation unit of the endoscope. Therefore, it is not required to connect the light source and the power source which are separately configured in the prior art, through a light conductor cable, and the power source is not required to be independently prepared. As a result, when only the endoscope is prepared, it is possible to immediately use the endoscope anywhere. Since no light conductor cable connected to the light source is used, no restriction is imposed on the aid work. Furthermore, the insertion unit and the operation unit are detachably coupled with each other. Even when the insertion unit is broken, therefore, the endoscope can be again used only by replacing the insertion unit with a normal one, so that the damage can be suppressed even more. Even in the case where an endotracheal tube is to be inserted on many patients by using the endoscope, infection of germs can be prevented from occurring, only by replacing the insertion unit with another one, with the result that perfect treatment can be rapidly performed.

In the endoscope of the present invention, a proximal end portion of the image transmitting optical fiber bundle of the insertion unit which is on the side of the operation unit is coaxial with the eyepiece of the operation unit. Therefore, an image of an object which is guided through the image transmitting optical fiber bundle can be observed more clearly via the eyepiece.

In the endoscope of the present invention, the coupling unit has a pressing member which causes a proximal end portion of the image transmitting optical fiber bundle of the insertion unit which is on the side of the operation unit, to be coupled under a condition where the proximal end portion is pressed toward the eyepiece of the operation unit. When the insertion unit is detachably coupled with the operation unit, therefore, the insertion unit can be firmly coupled and an image can be stably observed.

In the endoscope of the present invention, at least one of the distal ends of the illumination light transmitting optical fiber bundle, the image transmitting optical fiber bundle, or the wire is integrally bonded together by a resin at the distal end of the insertion unit. Therefore, a pedestal for fixing the fiber bundles and the wire to the distal end portion can be omitted, and the components can be simultaneously fixed. As a result, the number of parts can be reduced and the assembling work can be facilitated.

In the endoscope of the present invention, the resin tube is configured into a multi-lumen structure having at least two, or larger and smaller inner spaces, the illumination light transmitting optical fiber bundle and the image transmitting optical fiber bundle are passed through the larger inner space, and the wire is passed through the smaller inner space. Therefore, the distal ends of the fiber bundles can be firmly supported and fixed to the inner peripheral wall of the larger inner space. The wire is slidably supported on the inner peripheral wall of the smaller inner space. When the wire is pulled or slackened in order to bend the distal end of the insertion unit, therefore, The slack such as a meander of the wire in the middle is suppressed so that the endoscope has an excellent bending performance, with the result that the observation of the body cavity by means of the endoscope can be satisfactorily performed.

In the endoscope of the present invention, the surface of the distal end of the insertion unit is protected against clouding. For example, the surface of the distal end of the insertion unit is coated with anti-clouding material. The other example is that the anti-clouding membrane which is integrally molded with the resin is disposed at the distal end of the insertion unit. Therefore, the anti-clouding membrane is not peeled off from the distal end of the insertion unit, thereby preventing the distal ends of the illumination light transmitting optical fiber bundle and the image transmitting optical fiber bundle from clouding. As a result, a stable image can be obtained.

In the endoscope of the present invention, the distal end of the image transmitting optical fiber bundle is integrally bonded by a resin at the distal end of the insertion unit through a pipe in which a lens is integrally concentrically molded by a resin. Therefore, the endoscope can be produced at a lower cost than a prior art endoscope having an objective optical system in which a pipe and a lens are separated from each other at the distal end of an image transmitting optical fiber bundle.

In the endoscope of the present invention, the wire for bending the distal end of the insertion unit is made of a resin. Therefore, the endoscope can be produced at a lower cost than a prior art endoscope which uses a wire rope configured by thin wires of a metal such as stainless steel.

DETAILED DESCRIPTION OF THE PREFERRED EMBODIMENTS

Figure 1A:
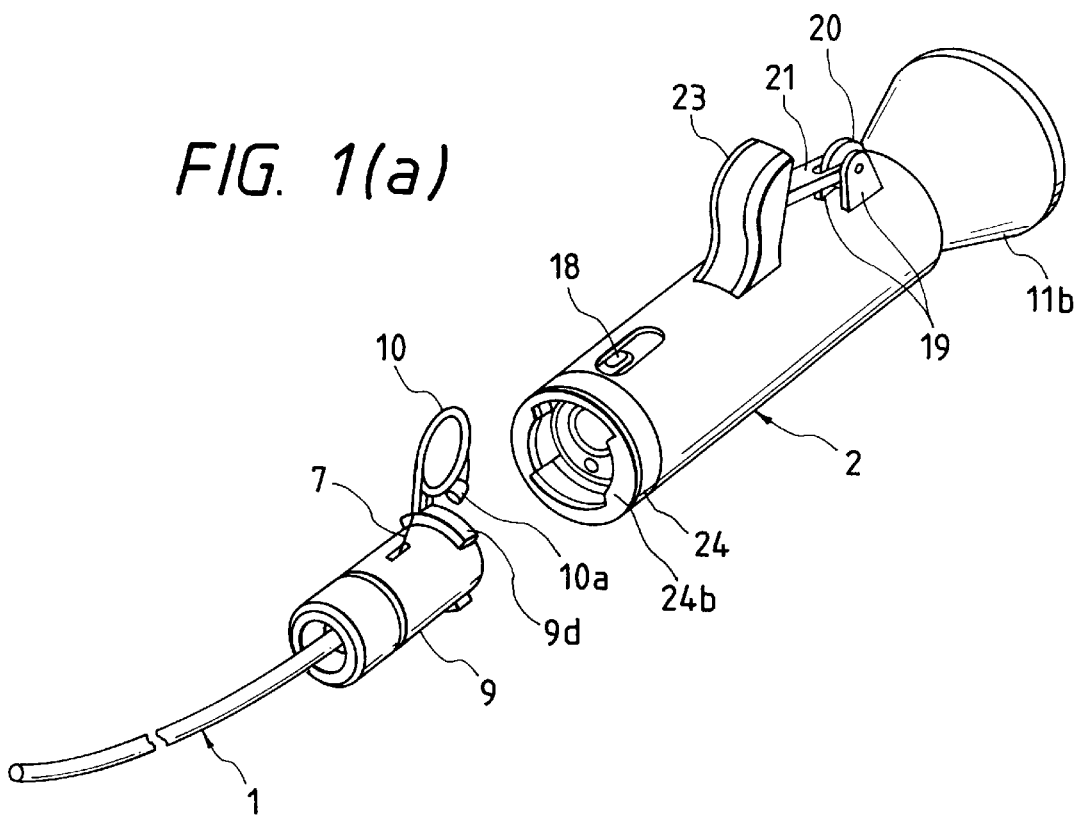
FIGS. 1(a) and 1(b) are external perspective views showing the disassembled and connected configurations of an embodiment of the endoscope.
Figure 2:
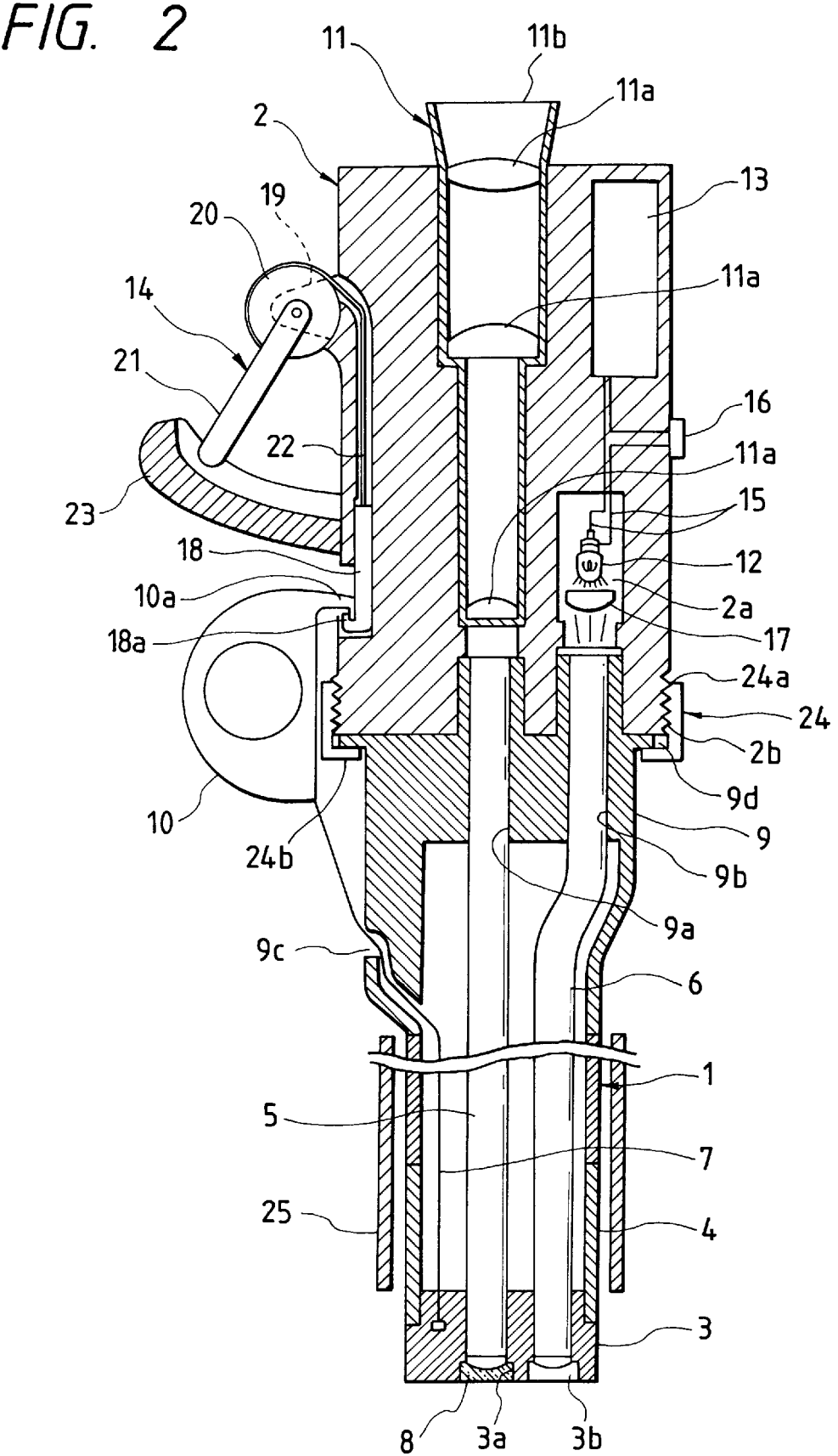
FIG. 2 is a longitudinal section view taken in the axial direction and schematically showing the internal configuration of FIG. 1(a)

Hereinafter, an embodiment of the endoscope of the invention will be described with reference to the accompanying drawings. FIGS. 1(a) and (b) are an external perspective view showing the configuration of a first embodiment of the invention, and FIG. 2 is a longitudinal section view taken in the axial direction and schematically showing the internal configuration of FIGS. 1(a) and (b).

Referring to FIGS. 1(a) and (b) and 2, the endoscope of the embodiment consists of an insertion unit 1 and an operation unit 2 which are detachably coupled with each other. The insertion unit 1 is a portion which is to be inserted into the trachea of a living body, and formed into a tubular shape which is flexible and hollow. A distal hard portion 3 is disposed at the distal end of the insertion unit. A flexible bending portion 4 is disposed so as to be continuous from the distal hard portion 3. An image transmitting optical fiber bundle 5, an illumination light transmitting optical fiber bundle 6, and a bending operation wire 7 are incorporated in the inner space of the insertion unit 1 so as to be elongated substantially parallel with the axial direction.

Distal ends of the image transmitting optical fiber bundle 5 and the illumination light transmitting optical fiber bundle 6 are connected to openings 3a and 3b which are formed so as to pass through the distal hard portion 3, respectively. A lens 8 for forming an image is mounted on the opening 3a to which the image transmitting optical fiber bundle 5 is connected. A substantially cylindrical connecting portion 9 is integrally concentrically attached to the proximal end of the insertion unit 1 on the side of the operation unit 2 which will be described later. Openings 9a and 9b are formed so as to pass through the proximal closed end face of the connecting portion 9 on the side of the operation unit 2. The proximal ends of the image transmitting optical fiber bundle 5 and the illumination light transmitting optical fiber bundle 6 on the side of the operation unit 2 are connected to the openings 9a and 9b, respectively.

The distal end of the bending operation wire 7 is fixed to the distal hard portion 3. The proximal end of the wire is pulled out to the outside of adjacent the connecting portion 9 through a hole 9c formed in the peripheral wall of the connecting portion 9, and then connected to a hook 10 which is half-annular and is disposed on the outer periphery of the connecting portion 9 so as to be reciprocally movable in the axial direction. A latch 10a which can be engaged with a hole 18a of the operation unit 2 is integrally formed in a proximal end portion of the hook 10 on the side of the operation unit 2. The hole of the operation unit will be described later.

The operation unit 2 is formed into a substantially cylindrical shape which can be gripped. In the operation unit 2, an eyepiece optical system 11 serving as the eyepiece, an illuminating lamp 12 serving as the light source, and a battery 13 serving as the power source for supplying a power to the lamp 12 are disposed. A bending operation unit 14 is disposed on the outer periphery of the operation unit 2. The bending operation unit 14 serves as the wire operating mechanism which produces and relaxes tension in the bending operation wire 7 so that the bending portion 4 of the insertion unit 1 bends.

The eyepiece optical system 11 is passed through the operation unit 2 in the axial direction. Three lenses 11a are arranged on the optical axis, and a finder 11b is disposed at the opening on the side opposite to the insertion unit 1. The lamp 12 is housed in a recess 2a which opens on the side of the insertion unit 1, and electrically connected to the battery 13 through lead wires 15. A switch 16 is connected in the circuit configured by the lead wires 15, and projected from the outer periphery of the operation unit 2. When the switch 16 is closed, the lamp 12 is powered to emit illumination light. A dry battery or a rechargeable battery is used as the power source. The reference numeral 17 designates a lens which is located on the optical axis of the lamp 12 and converges light emitted from the lamp 12 toward the opening of the recess 2a.

The bending operation unit 14 consists of: a catch 18 which is supported in the vicinity of the outer periphery of the operation unit 2 so as to be movable in the axial direction; a pulley 20 which is rotatably supported by a pair of brackets 19 projected from the outer periphery of the operation unit 2; and a lever 21 in which proximal end is fixed to the pulley 20. A hole 18a is formed at distal end of the catch 18 on the side of the insertion unit 1. When the insertion unit 1 is coupled with the operation unit 2 by the method described later, the latch 18a is engaged with the latch 10a of the hook 10 disposed on the insertion unit 1. The distal end of a wire 22 is connected to proximal end of the catch 18 on the side opposite to the insertion unit 1. The proximal end of the wire 22 is wound on the pulley 20 and fixed thereto. When the lever 21 is turned, the catch 18 is reciprocated in the axial direction through the pulley 20 and the wire 22, so as to produce and relax tension in the wire 7 through the hook 10, thereby causing the bending portion 4 to bend. The reference numeral 23 designates a lever guide which is projected from the outer periphery of the operation unit 2 and formed into an arcuate shape about the rotation axis of the pulley 20.

Next, the structure of the coupling unit which couples the insertion unit 1 with the operation unit 2 will be described.

The coupling unit 24 is formed into a substantially cylindrical shape. An internal thread 24a is formed on the inner periphery of the coupling unit. The internal thread is to be engaged with an external thread 2b formed on the outer periphery of the distal end portion of the operation unit 2 on the side of the insertion unit 1. A pair of right and left sector projections 24b are integrally formed on the distal end face of the coupling unit 24 opposing the insertion unit 1. On the other hand, in the insertion unit 1, a pair of sector projections 9d which can be inserted between the projections 24b of the coupling unit 24 are integrally formed on the outer periphery of the proximal end portion of the connecting portion 9 on the side of the operation unit 2. The image transmitting optical fiber bundle 5 and the illumination light transmitting optical fiber bundle 6 which are passed through the connecting portion 9 are positioned so as to be respectively matched with the hole of the eyepiece optical system 11 passed through the operation unit 2, and the recess 2a in which the illuminating lamp 12 is housed.

Next, the procedure of using the thus configured endoscope for inserting an endotracheal tube of the embodiment will be described. First, the projections 9d of the connecting portion 9 of the insertion unit 1 are inserted into the recess between the projections 24b of the coupling unit 24. Then, the proximal ends of the image transmitting optical fiber bundle 5 and the illumination light transmitting optical fiber bundle 6 which protrude from the proximal end face of the connecting portion 9 on the side of the operation unit 2 are inserted into the hole of the eyepiece optical system 11 of the operation unit 2, and the recess 2a for the illuminating lamp 12, respectively. The coupling positions are preset so that the fiber bundles are connected to the respective components on the same optical axis. Thereafter, the coupling unit 24 is coupled with the operation unit 2 by means of the threads, and the proximal end face of the connecting portion 9 is pressingly contacted with the distal end of the operation unit 2. This coupling is conducted so that the projections 9d of the connecting portion 9, and the projections 24b of the coupling unit 24 are overlapped with each other.

Figure 3:
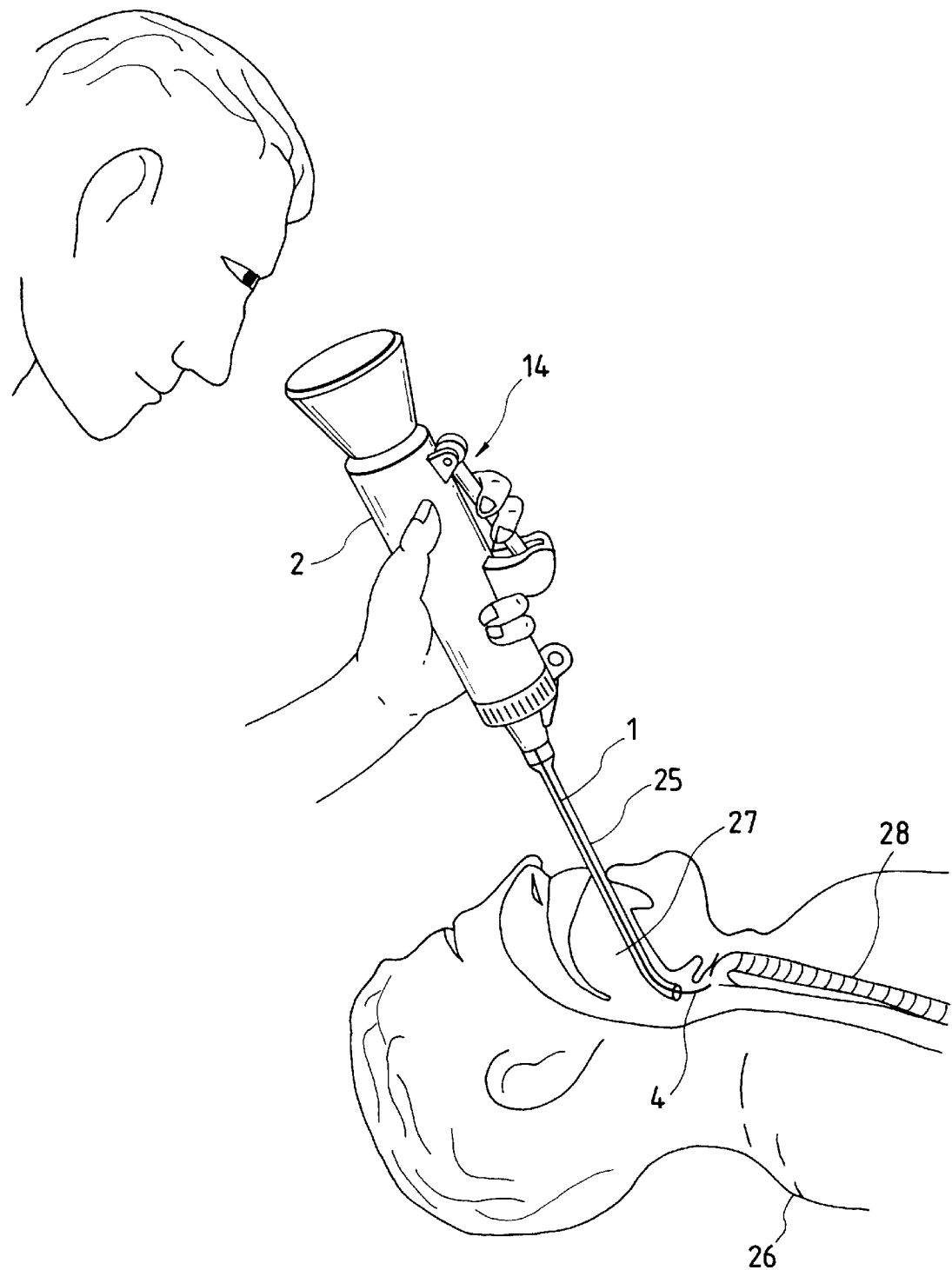
FIG. 3 is a diagram showing a state where an endotracheal tube is inserted by using the endoscope shown in FIG. 1.
Figure 4A:
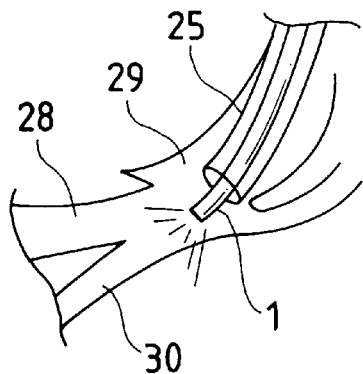
FIGS. 4(a) to 4(c) are diagrams showing the procedure of the intubation of FIG. 3.
Figure 4B:
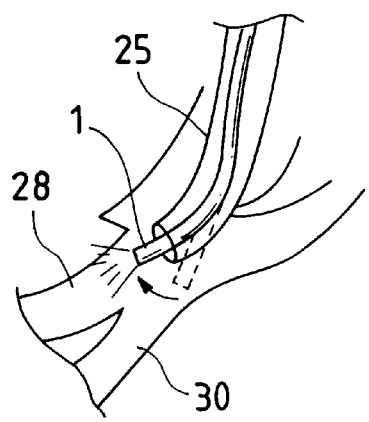
Figure 4C:
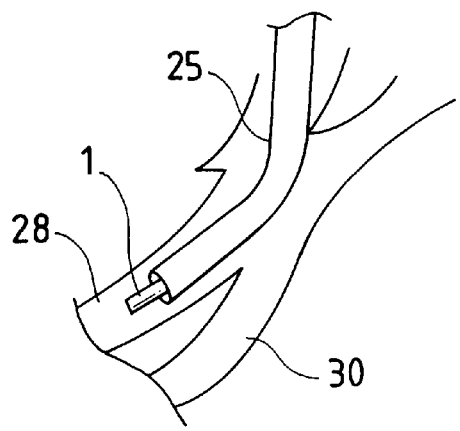

Thereafter, the insertion unit 1 is inserted into the inner space of an endotracheal tube 25 which is to be inserted, and set so that the distal end is slightly projected from the distal end of the endotracheal tube 25. The switch 16 of the operation unit 2 is depressed so that the illuminating lamp 12 is turned on. Under this state, as shown in FIG. 3, the insertion unit 1 is inserted into the oral cavity 27 of a patient 26, and the bending operation unit 14 is operated so that the bending portion 4 bends. The insertion unit 1 is inserted into the trachea 28 while observing the body cavity. Next, the endotracheal tube 25 is inserted into the trachea 28 with using the insertion unit 1 as a guide, and caused to stay therein. Finally, the insertion unit 1 is pulled out. FIG. 4(a) shows a state where the distal end of the insertion unit 1 is inserted through the oral cavity 27 into the pharynx 29, FIG. 4(b) shows a state where the bending operation unit 14 is operated and the distal end of the insertion unit 1 is bent toward the trachea 28, and FIG. 4(c) shows a state where the distal end of the insertion unit 1 is inserted into the trachea 28 and the endotracheal tube 25 is inserted into the trachea 28 with using the insertion unit 1 as a guide. The reference numeral 30 designates the esophagus.

In the embodiment, the illuminating lamp 12 and the battery 13 are incorporated in the operation unit 2 of the endoscope. A light conductor cable for connecting the light source and the operation unit with each other is not required. Such a light conductor cable is required in the case where the light source and the operation unit are separately configured.

When only the endoscope is prepared, furthermore, it is possible to use the endoscope anywhere without preparing a separate power source. Since a light conductor cable or a cord connected to the light source is not used, no restriction is imposed on the work. Even when a person is injured due to an accident or a disaster or suddenly attacked with a disease, therefore, the endotracheal tube 25 can be inserted into the trachea 28 safely, surely, and rapidly.

The insertion unit 1 and the operation unit 2 are detachably coupled with each other through the coupling unit 24. Even when, for example, the insertion unit 1 is stamped in a confused location and broken, therefore, it is required to replace only the insertion unit 1 with a normal one, thereby suppressing the damage even more. Even in the case where the endotracheal tube 25 is to be inserted on many patients, furthermore, treatment which is safe or free from infection of germs or the like can be rapidly performed only by replacing the insertion unit 1 with another one.

The proximal end portion of the image transmitting optical fiber bundle 5 of the insertion unit 1 on the side of the operation unit, and the eyepiece optical system 11 of the operation unit 2 are coaxially disposed, and the proximal end portion of the image transmitting optical fiber bundle 5 of the insertion unit 1 on the side of the operation unit is coupled under a pressed condition with the distal end portion of the operation unit 2 in which the insertion unit is to be coupled, by the coupling unit 24 serving also as the pressing member. Therefore, the insertion unit 1 can be firmly coupled with the operation unit 2, with the result that the observation performance can be stably improved. When the lever 21 of the bending operation unit 14 is pressed by fingers used for gripping the operation unit 2, both the operations of gripping the operation unit 2 and bending the bending portion 4 can be conducted with one hand, and hence the workability is improved.

When the thus configured endoscope for inserting an endotracheal tube is used, the endotracheal tube 25 can be easily inserted into the trachea 28 without backwardly tilting the head of the patient 26, as shown in FIG. 3.

In the above, an example of the configuration of the coupling unit 24 of the embodiment has been described. The invention is not limited to this. As shown in a second embodiment of FIGS. 5 and 6, for example, the coupling unit 24 which is to be coupled by means of threads may be omitted, and a circular hole portion 2c of a predetermined depth may be formed concentrically on the distal end face of the operation unit 2 on the side of the insertion unit. A pair of sector projections 2d are formed on the inner periphery of the distal end face of the hole portion 2c so as to oppose each other. The inner diameter of the projections 2d is equal to the outer diameter of the connecting portion 9 of the insertion unit 1. The pair of sector projections 9d disposed on the outer periphery of the proximal end portion of the connecting portion 9 on the side of the operation unit have a shape which can be inserted between the projections 2d of the operation unit. The thickness in the axial direction of the projections 2d is gradually increased in the circumferential direction, or the projections have a tapered shape.

Figure 5:
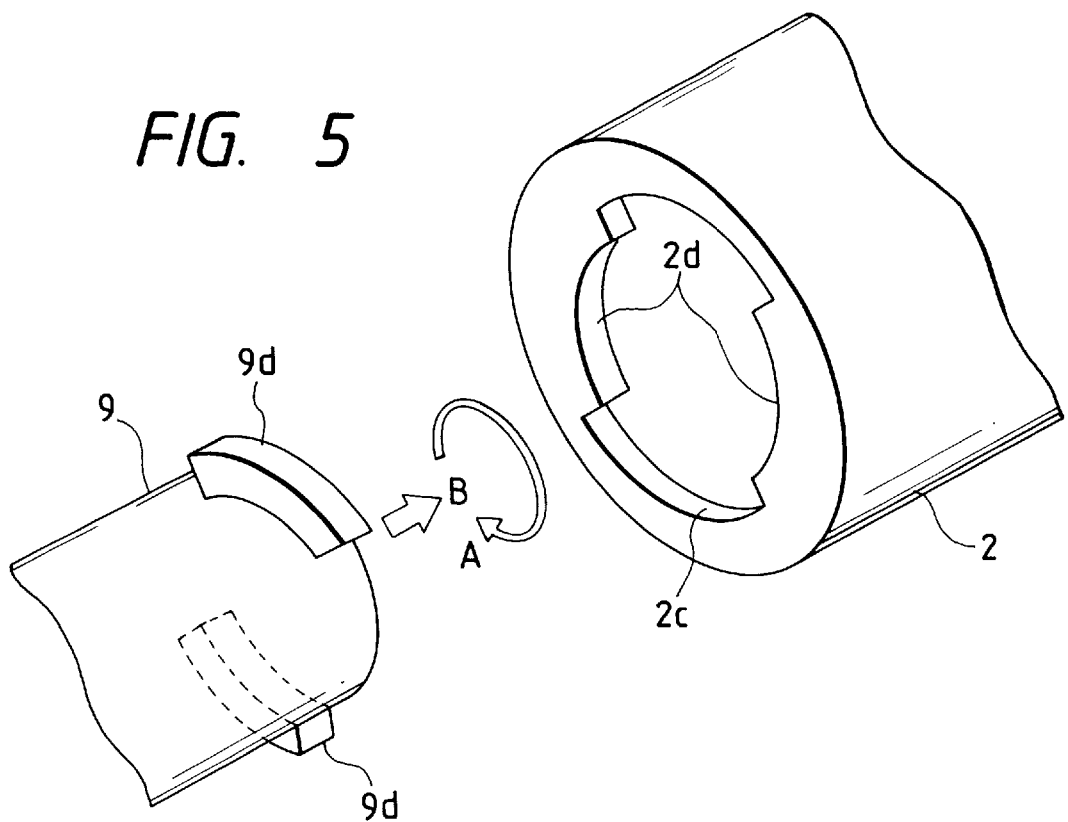
FIG. 5 is a perspective view showing the configuration of the coupling unit in a second embodiment of the invention.
Figure 6:
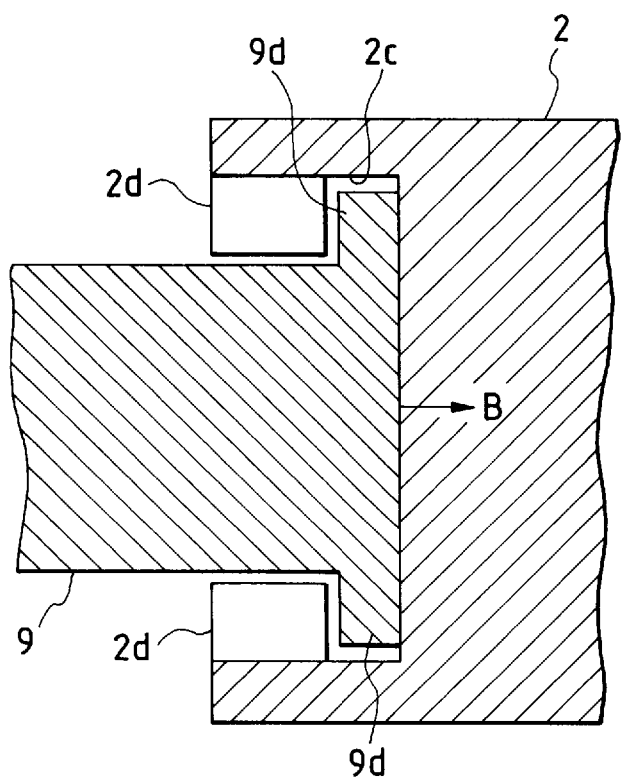
FIG. 6 is a longitudinal section view of the coupling unit of FIG. 5.

In the above-described configuration, the projections 9d of the connecting portion 9 are inserted between the projections 2d of the operation unit 2, and then rotated in the direction of the arrow A in FIG. 5. As a result, in accordance with the variation of the projections 9d of the connecting portion 9, the proximal end face of the connecting portion 9 is pressed against the bottom face of the hole portion 2c of the operation unit 2 in the direction of the arrow B, as shown in FIG. 6. and fastened and fixed. In this case, a positioning mechanism such as a ball plunger may be required in order to respectively coincide the optical axis of the fiber bundles 5 and 6 with those of the eyepiece optical system 11 and the lamp 12 of the operation unit 2.

Figure 7:
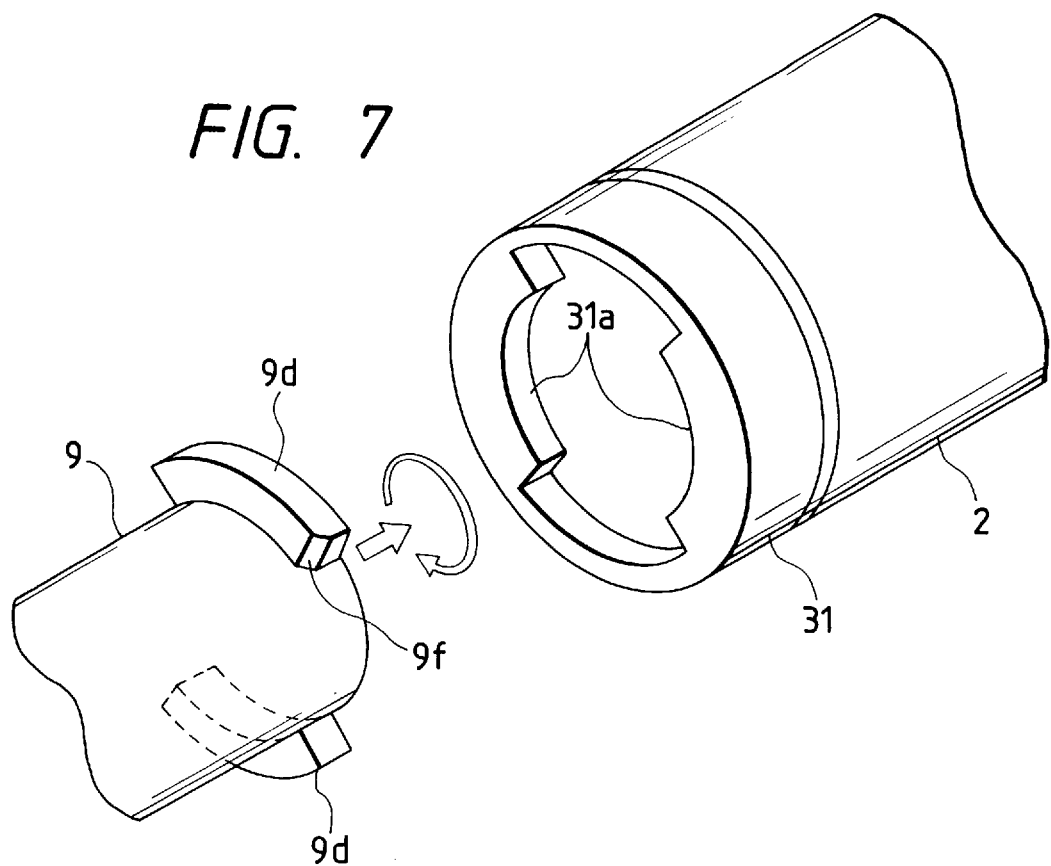
FIG. 7 is a perspective view showing the configuration of the coupling unit in a third embodiment of the invention.
Figure 8:
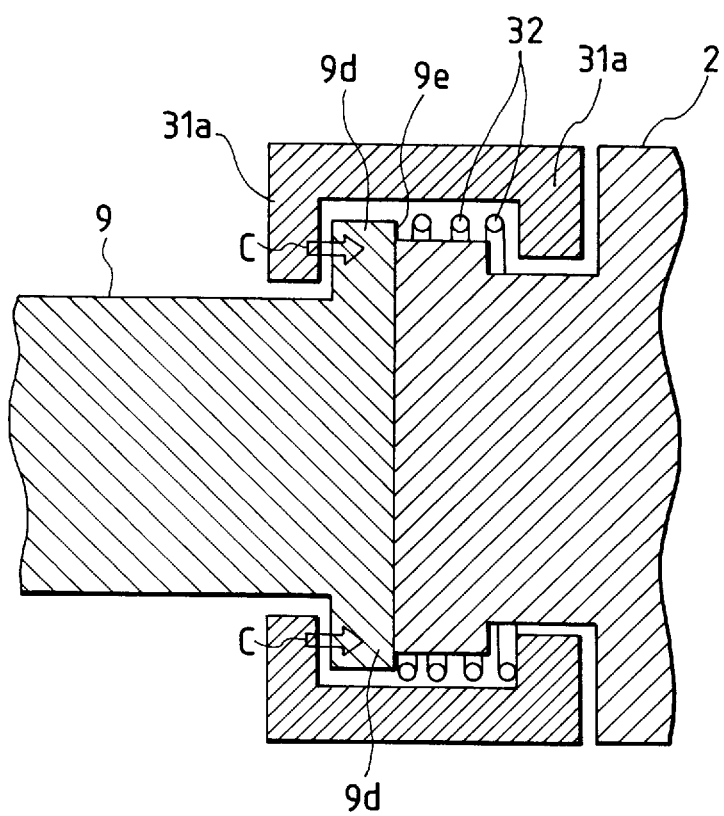
FIG. 8 is a longitudinal section view of the coupling unit of FIG. 7.

FIGS. 7 and 8 show the configuration of a third embodiment of the coupling unit 24. In the embodiment, a pair of sector projections 31a which are inwardly projected are formed on each of the distal end faces of an annular coupling unit 31. The coupling unit 31 is attached to the distal end portion of the operation unit 2 on the side of the insertion unit. Distal end of a compression coil spring 32 is fixed to the outer periphery of the distal end portion of the operation unit 2 on the side of the insertion unit. The proximal end of the spring abuts against the inner faces of the projections 31a of the coupling unit 31 on the side of the operation unit.

A cutaway portion 9f is formed on each of the projections 9d. In this configuration, when the projections 9d of the connecting portion 9 are inserted between the projections 31a of the coupling unit 31, the connecting portion 9 can be rotated against the urging force of the spring 32 so as to forcedly enter between the projections and the operation unit. After the insertion, the outer projections 31a of the coupling unit 31 are caused by the urging force of the spring 32 to press the projections 9d of the connecting portion 9 in the direction of the arrow C, with the result that the proximal end face 9e of the connecting portion 9 is pressingly fixed to the distal end face of the operation unit 2.

Figure 9:
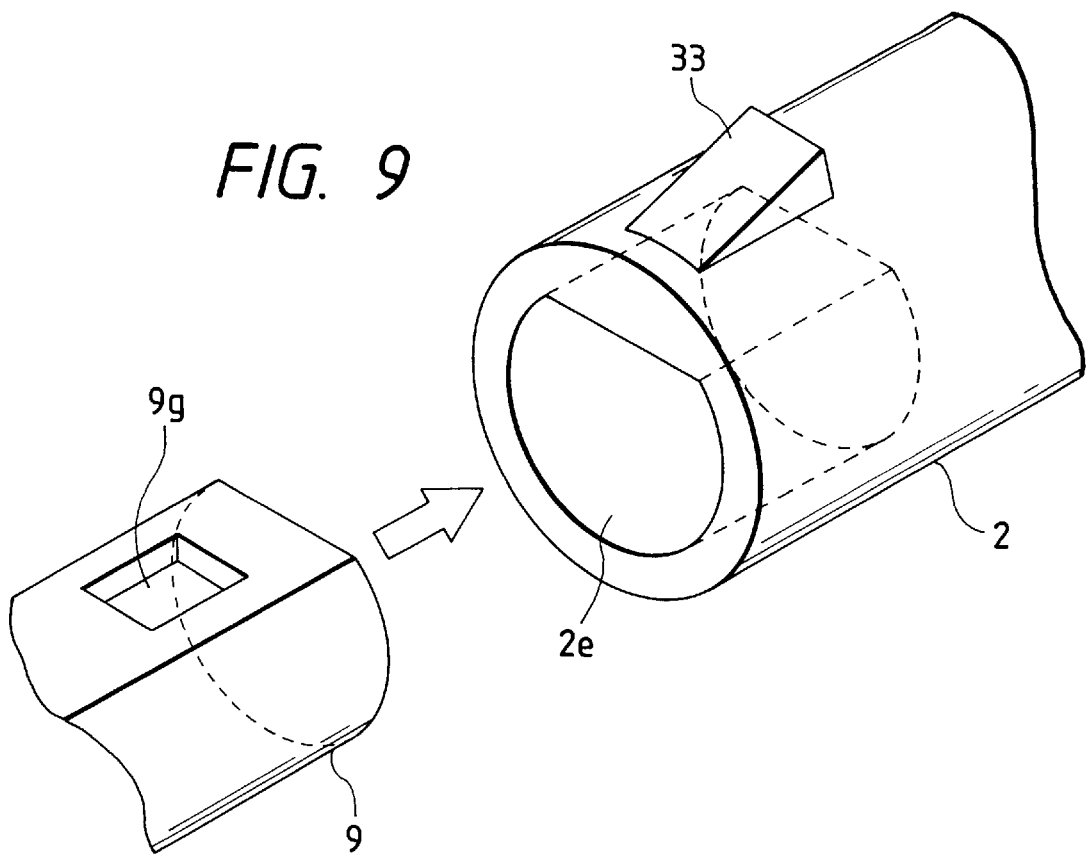
FIG. 9 is a perspective view showing the configuration of the coupling unit in a fourth embodiment of the invention.
Figure 10:
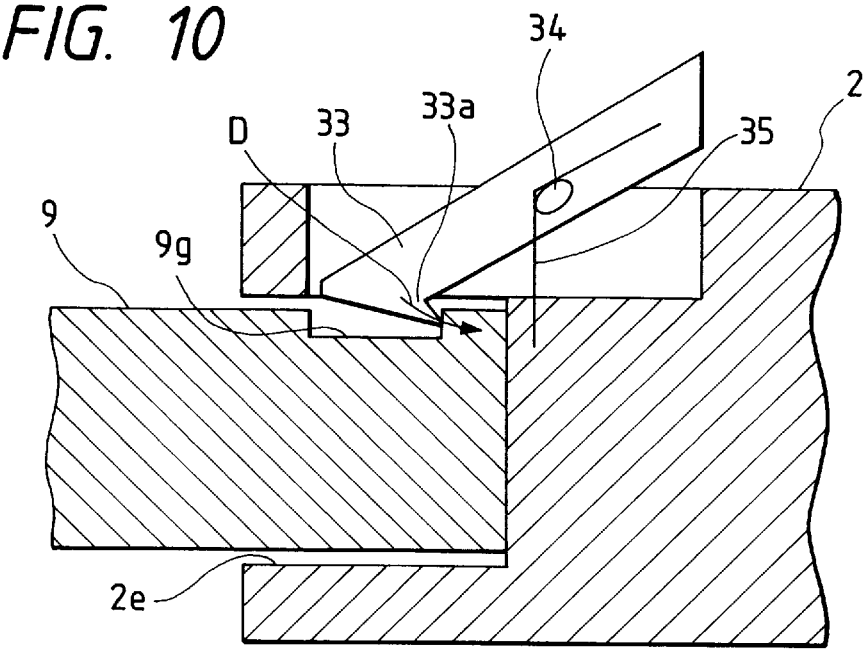
FIG. 10 is a longitudinal section view of the coupling unit of FIG. 9.
Figure 11:
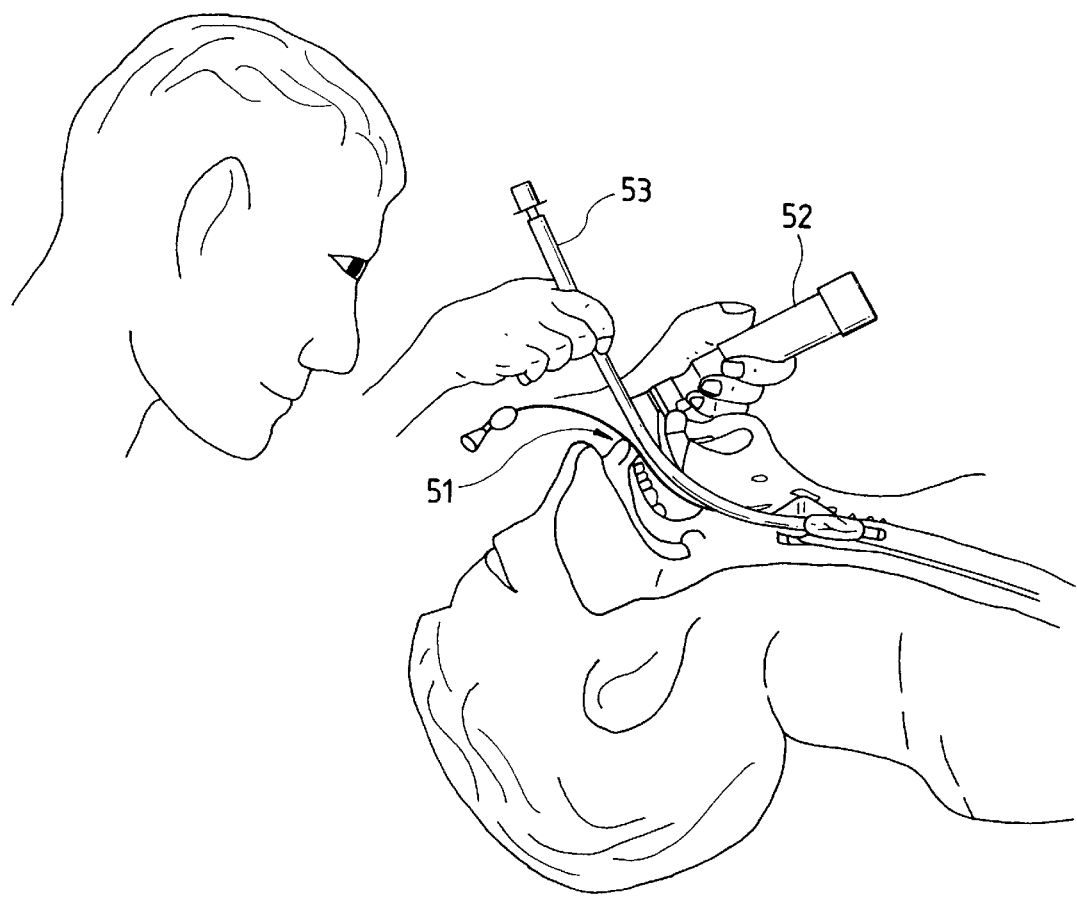
FIG. 11 is a diagram showing an example of a method of an oral endotracheal intubation in the conventional art.

FIGS. 9 and 10 show the configuration of a fourth embodiment of the coupling unit 24. In the embodiment, the annular coupling unit 24 is omitted, and the connecting portion 9 of the insertion unit 1 is connected with the operation unit 2 by means of a lever 33 disposed on the operation unit 2. The connecting portion 9 has a substantially semicircular section shape. A substantially semicircular recess 2e into which the connecting portion 9 is to be fitted is formed in the distal end face of the operation unit 2 on the side of the insertion unit, so as to have a predetermined depth. A rectangular engaging hole 9g is formed in the flat portion of the outer periphery of the connecting portion 9. The lever 33 is rotatably attached to the outer periphery of the operation unit 2 through a support shaft 34 so as to oppose the flat portion of the inner periphery of the recess 2e. A hook 33a is disposed at distal end of the lever 33 and inwardly projected from the flat portion of the inner periphery of the recess 2e. The lever 33 is rotatively urged in the direction of the arrow D by a coil spring 35 attached to the support shaft 34.

In the above-described configuration, when the connecting portion 9 of the insertion unit 1 is inserted into the recess 2e of the operation unit 2, the hook 33a at the distal end of the lever 33 is caused by the urging force of the coil spring 35 to press one side of the engaging hole 9g on the side of the operation unit 2, whereby the proximal end face of the connecting portion 9 is pressed against the bottom face of the recess 2e of the operation unit 2 so as to be fixed thereto.

Figure 1B:
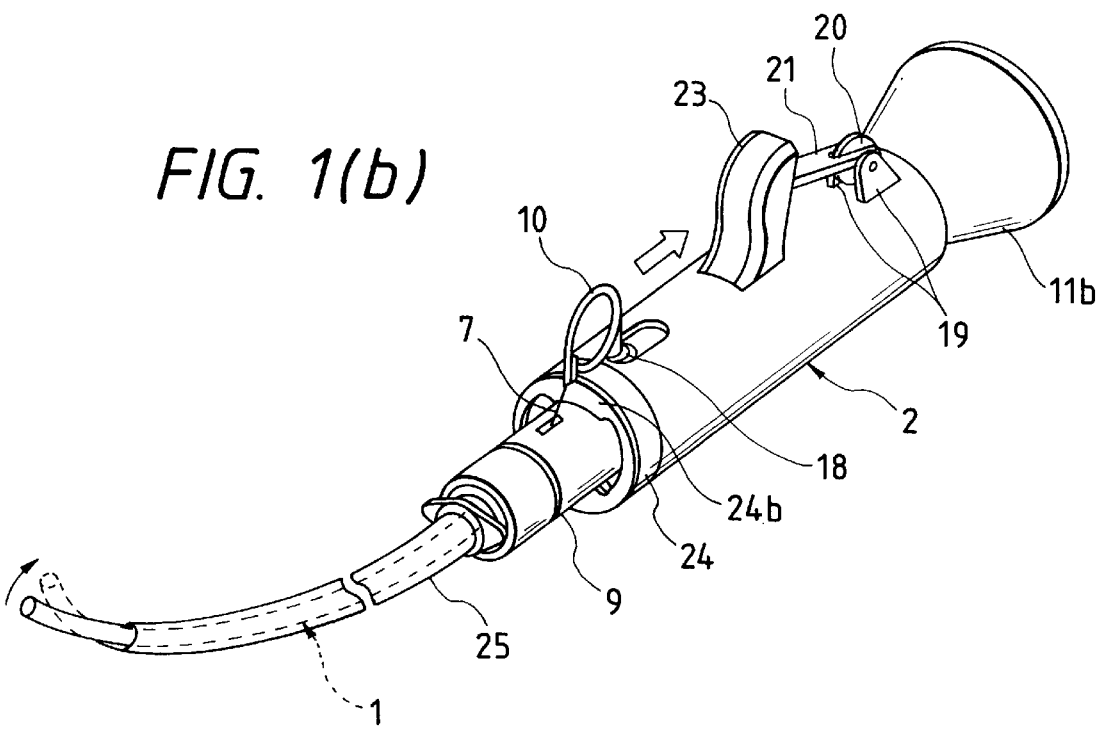

Also the configuration of the bending operation unit 14 shown in FIGS. 1 and 2 is an example. The invention is not limited to this, and the bending operation unit may be configured in another manner.

Figure 12:
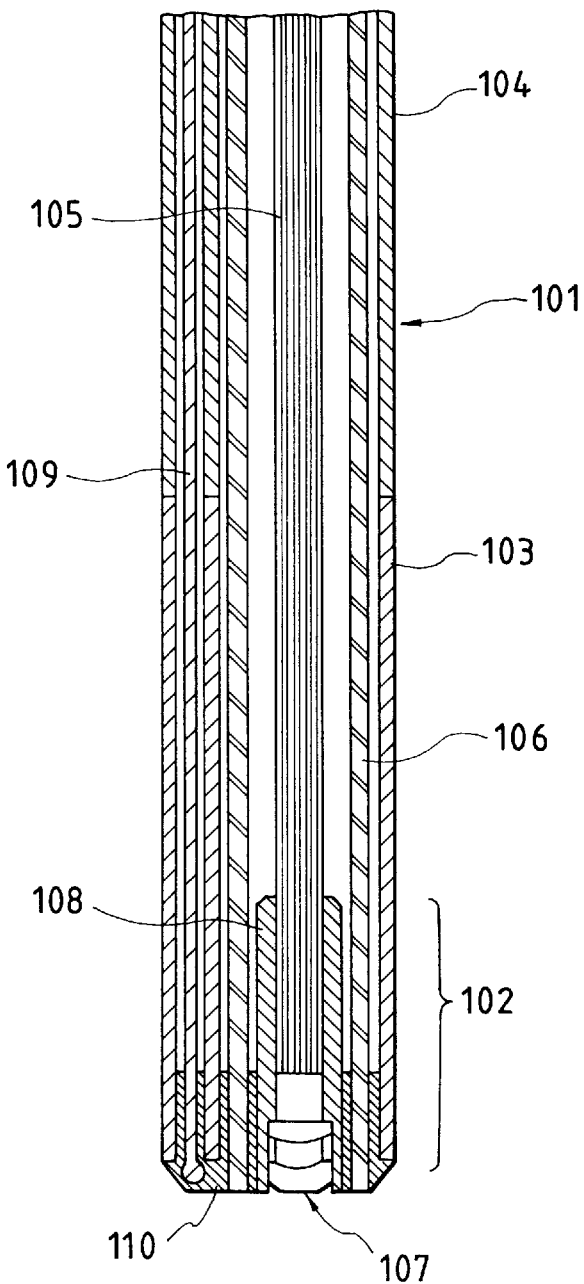
FIG. 12 is a longitudinal section view showing the configuration of a fifth embodiment of the endoscope of the invention.
Figure 13:
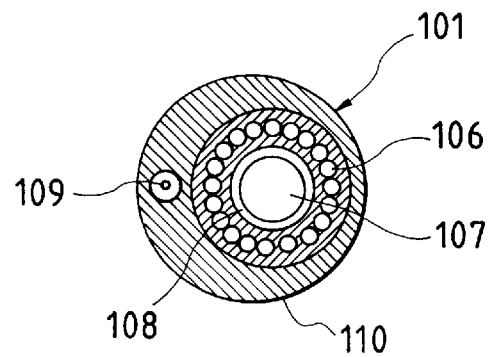
FIG. 13 is a front view of the distal end of the endoscope of FIG. 1.

FIG. 12 is a longitudinal section view showing the configuration of a fifth embodiment of the invention, and FIG. 13 is a front view of the distal end of the endoscope of FIG. 12.

Referring to FIGS. 12 and 13, an insertion unit 101 of the endoscope which is to be inserted into a living body is made of a resin and formed into a tubular shape. The insertion unit 101 is configured by a distal end hardened portion 102, a bending portion 103 serving as the bendable portion, and an intermediate conduit portion 104 in the sequence when started from the distal end. The bending portion 103 and the intermediate conduit portion 104 have a multi-lumen structure in which two, or larger and smaller inner spaces are passed in parallel in the axial direction. The bending portion 103 is more flexible than the intermediate conduit portion 104. An image transmitting optical fiber bundle 105 is passed through the center portion of the larger inner space. Illumination light transmitting optical fiber bundle 106 is passed over the outer periphery of the image transmitting optical fiber bundle 105 so as to surround the image transmitting optical fiber bundle. A pipe 108 which holds an objective optical system 107 having an objective lens is fitted onto the image transmitting optical fiber bundle 105, and fixed to the fiber bundle by an adhesive. The distal end of the illumination light transmitting optical fiber bundle 106 is located at the same level as the distal end of the objective optical system 107. A wire 109 configured by twisting resin fibers is passed through the smaller inner space of the multi-lumen tube.

Next, the configuration of the distal end hardened portion 102 will be described. First, the distal end faces of the objective optical system 107 and the illumination light transmitting oprical fiber bundle 106 which are at the same level are positioned so as to be slightly projected from the distal end face of the bending portion 103 of the resin tube. Then, a thicker portion is formed at the distal end of the wire 109 by forming a knot or heating the distal end. The thicker portion is positioned so as to be slightly projected from the distal end face of the resin tube. A resin 110 is supplied to the distal end face of the resin tube in such a manner that the resin is not supplied to the distal end face of the objective optical system 107 on the side of the distal end, and also to the distal end face of the illumination light transmitting optical fiber bundle 106. The resin 110 penetrates into gaps between the inner peripheries of the holes of the multi-lumen tube and the outer peripheries of the pipe 108, the illumination light transmitting optical fiber bundle 106, and the wire 109 which are passed through the holes, and then solidifies so as to firmly fix the objective optical system 107, the illumination light transmitting optical fiber bundle 106, and the wire 109 to the distal end of the resin tube. As a result, the distal end hardened portion 102 is configured.

In the embodiment, the distal ends of the illumination light transmitting optical fiber bundle 106, the image transmitting optical fiber bundle 105 to which the objective optical system 107 is attached at the distal end, and the wire 109 are integrally bonded together by the resin at the distal end of the insertion unit 101. Therefore, it is not required to dispose a part having a complicated shape and used for fixing the fiber bundles 105 and 106 and the wire 109, such as a pedestal at the distal end. The components including the wire 109 can be simultaneously fixed. As a result, the number of parts can be reduced and the assembling work can be facilitated.

The resin tube is configured into a multi-lumen structure having the two, or larger and smaller inner spaces, the illumination light transmitting optical fiber bundle 106 and the image transmitting optical fiber bundle 105 are passed through the larger inner space, and the wire 109 is passed through the smaller inner space. The distal ends of the fiber bundles 105 and 106 and the wire 109 are fixed to the distal end of the distal end hardened portion 102 by the resin 110. Therefore, the distal end portions of the fiber bundles 105 and 106 and the objective optical system 107 are firmly supported and fixed to the inner peripheral wall of the larger inner space. The wire 109 is passed through the smaller inner space. When the wire 109 is pulled or slackened in order to bend the distal end of the insertion unit, therefore, the slack such as a meander of the wire 109 in the middle is suppressed so that the endoscope has an excellent bending performance, with the result that the observation of the body cavity by means of the endoscope can be satisfactorily performed.

Since the wire 109 is configured by twisting resin fibers, the endoscope can be produced at a lower cost than a prior art endoscope which uses a wire rope configured by thin wires of a metal such as stainless steel. Furthermore, the adhesive strength can be enhanced by fixing the distal end of the wire 109 by using the resin.

Figure 14:
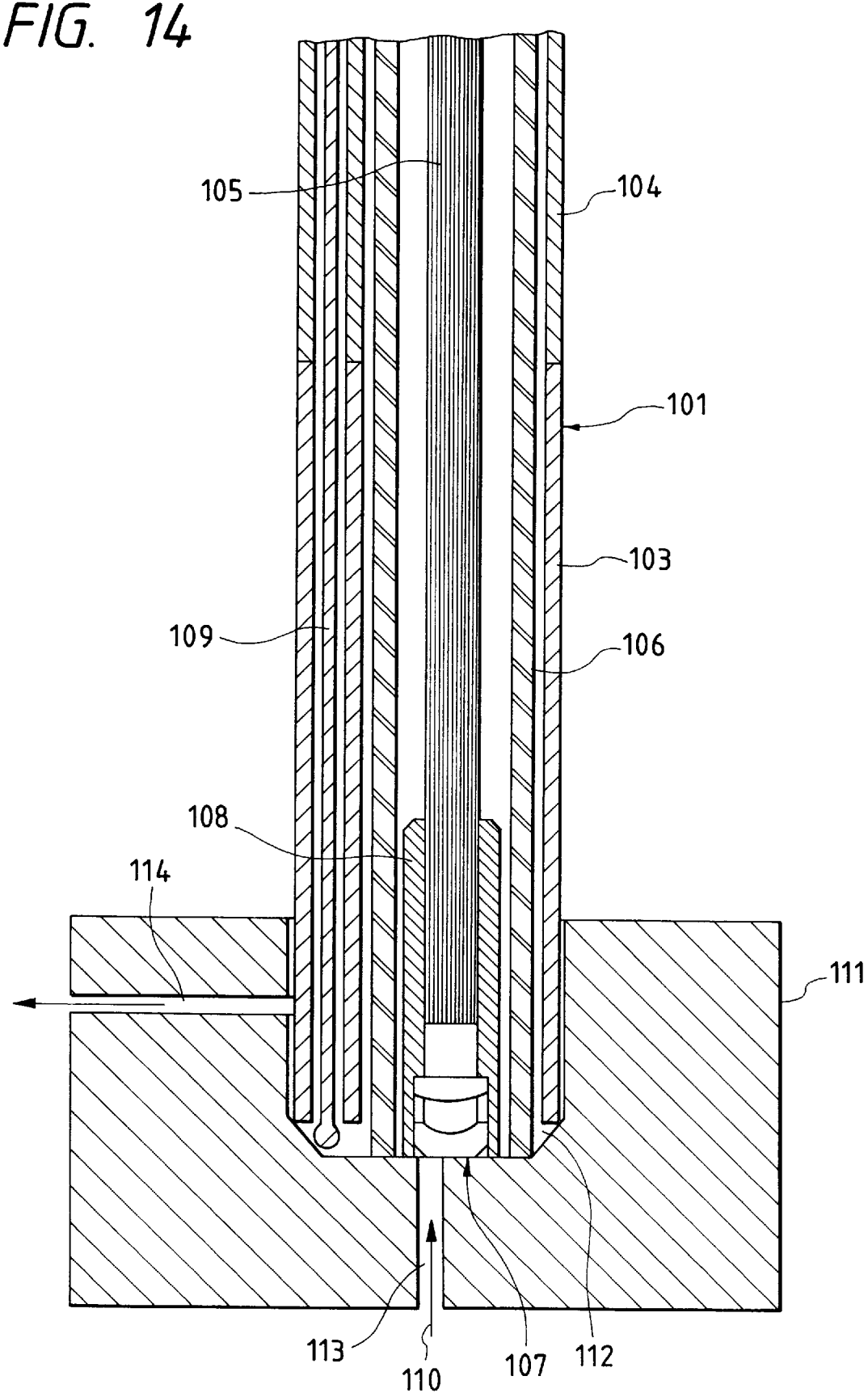
FIG. 14 is a diagram showing an example of a method of producing the distal end of the insertion union of the endoscope of FIG. 1.

In the embodiment described above, in order to fix the distal ends of the pipe 108, the illumination light transmitting optical fiber bundle 106, and the wire 109, the resin 110 is manually supplied to the distal end of the insertion unit 101. Alternatively, a mold 11 such as shown in FIG. 14 may be used. A recess 112 is formed in the upper face of the mold 111. The recess has a circular section shape and has an inner diameter which is equal to the outer diameter of the insertion unit 101. An inlet 113 which opens at the center of the bottom face of the recess 112 is formed in the lower face of the mold 111 so as to pass through the mold. An outlet 114 which opens at a position of a predetermined depth on the inner peripheral face of the recess 112 is formed in the side face of the mold 111 so as to pass through the mold.

The distal end of the insertion unit 101 is fixed by a resin by using the mold 111 in the following manner. The distal end of the insertion unit 101 in which the pipe 108, the illumination light transmitting optical fiber bundle 106, and the wire 109 are set to the distal end is inserted into the recess 112 of the mold 111. The resin 110 is then poured through the inlet 113. After the level of the poured resin 110 reaches the height of the outlet 114, the resin 110 flows out through the outlet 114 even when the resin 110 is further poured, so that the level of the resin 110 becomes equal to the height of the outlet 114, with the result that the level of the resin 110 can be controlled so as to be constant. Alternatively, the outlet 114 may be omitted and the amount of the poured resin 110 may be controlled. The extra resin 110 adhering to the distal end face of the insertion unit 101 is removed away by grinding.

Figure 15:
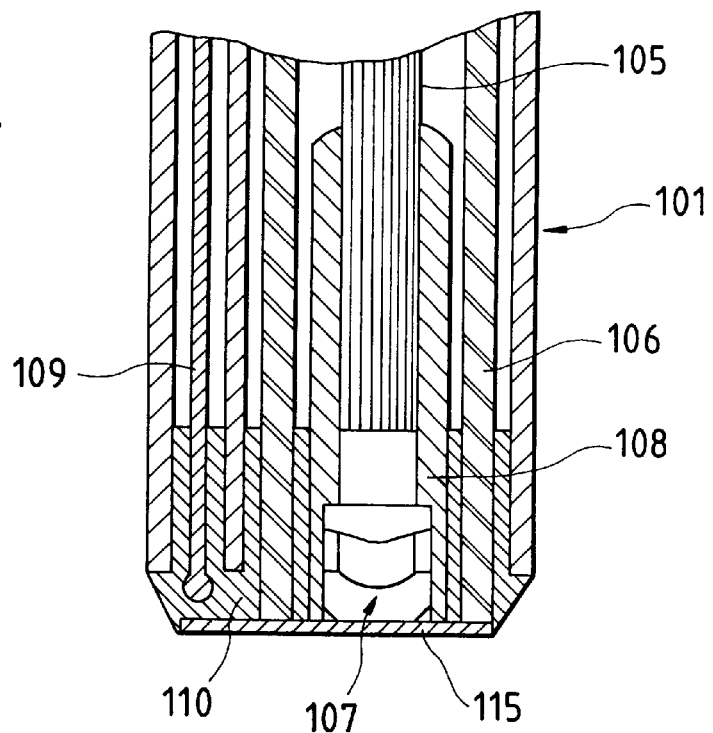
FIG. 15 is a longitudinal section view showing the configuration of the distal end of an insertion unit in a sixth embodiment of the endoscope of the invention.

FIG. 15 shows the configuration of the distal end of the insertion unit 101 in a sixth embodiment of the invention. In the embodiment, an anti-clouding membrane 115 is integrally molded on the entire surface of the distal end of the insertion unit 101.

In the embodiment, since the anti-clouding membrane 115 is disposed at the entire surface of the distal end of the insertion unit 101, the distal ends of the objective optical system 107 and the illumination light transmitting optical fiber bundle 106 are prevented from clouding, with the result that a stable image can be obtained. In the prior art, when a metal pedestal is used, an anti-clouding membrane must be bonded to the pedestal by an adhesive, and hence there arises a problem in that the anti-clouding membrane is easily peeled off. The configuration in which the anti-clouding membrane 115 is integrally molded with the resin 110 can solve the problem.

Figure 16:
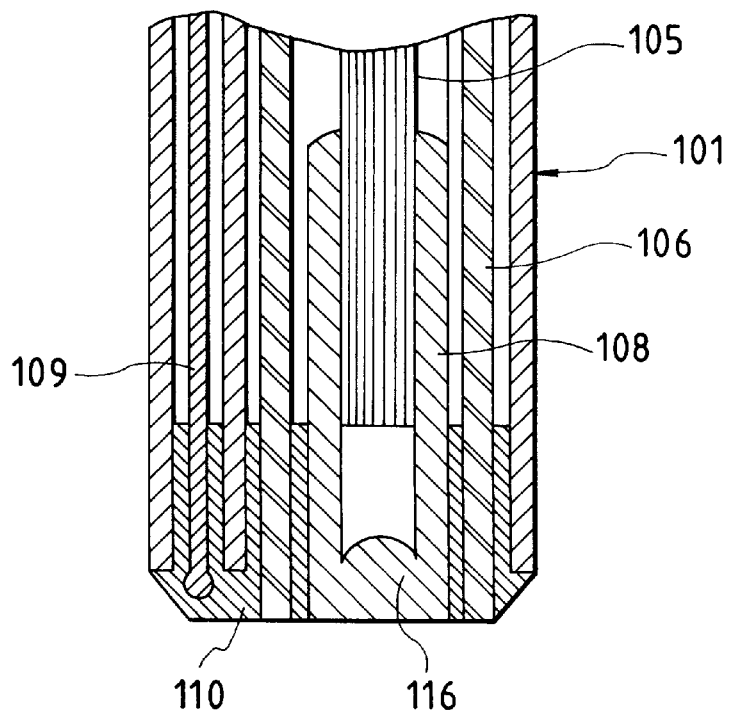
FIG. 16 is a longitudinal section view showing the configuration of the distal end of an insertion unit in a third embodiment of the endoscope of the invention.

FIG. 16 shows the configuration of the distal end of the insertion unit 101 in a third embodiment of the invention. In the embodiment, the pipe 108 which holds the objective optical system 107 is made of a resin, and the lens 116 of the objective optical system 107 is formed by the resin so as to be integrated with the pipe 108. The configuration in which the pipe 108 and the lens 116 are integrally molded by a resin enables the endoscope to be produced at a lower cost.

As seen from the above description, in the endoscope of the invention, the light source and the power source are incorporated in the operation unit of the endoscope. Therefore, a light counductor cable for connecting a light source with a power source is not required. As a result, even when only the endoscope is prepared and a power source is not separately prepared, it is possible to immediately use the endoscope anywhere. Since no light conductor cable connected to the light source is used, no restriction is imposed on the work. Even when a person is injured due to an accident or a disaster or suddenly attacked with a disease, therefore, an endotracheal tube can be inserted safely, surely, and rapidly into the trachea.

The insertion unit and the operation unit are detachably coupled with each other through coupling unit. Even when, for example, the insertion unit is stamped in a confused location and broken, therefore, the endoscope can be reused only by replacing the insertion unit with a normal one, thereby suppressing the damage even more. Even in the case where insertion of the endotracheal tube is to be conducted on many patients, furthermore, treatment which is safe or free from infection of germs or the like can be rapidly performed only by replacing the insertion unit with another one.

The proximal portion of the image transmitting optical fiber bundle of the insertion unit on the side of the operation unit, and the eyepiece of the operation unit are coaxially disposed, and the proximal end portion of the image transmission optical fiber bundle of the insertion unit on the side of the operation unit is coupled under a pressed condition with the distal end portion of the operation unit in which the insertion unit is to be coupled, by the coupling unit serving also as the pressing member. Therefore, the insertion unit can be firmly coupled with the operation unit, with the result that the observation performance can be stably improved.

As seen from the above description, in the endoscope of the invention, the distal ends of the illumination light transmitting optical fiber bundle, the image transmitting optical fiber bundle, and the wire is integrally bonded together by a resin at the distal end of the insertion unit. Therefore, it is not required to dispose a part for fixing the fibers bundles and the wire, such as a pedestal at the distal end. The components including the wire can be simultaneously fixed. As a result, the number of parts can be reduced and the assembling work can be facilitated.

The insertion unit is configured into a multi-lumen structure having two, or larger and smaller inner spaces, the illumination light transmitting optical fiber bundle and the image transmitting optical fiber bundle are passed through the larger inner space, and the wire is passed through the smaller inner space. The distal ends of the fiber bundles and the wire are fixed to the distal end of the distal end hardened portion by a resin. Therefore, the distal end portions of the fiber bundle are firmly supported and fixed to the inner peripheral wall of the larger inner space. The wire is passed through the smaller inner space. When the wire is pulled or slackened in order to bend the distal end of the insertion unit, therefore, the slack such as a meander of the wire in the middle is suppressed so that the endoscope has an excellent bending performance, with the result that the observation of the body cavity by means of the endoscope can be satisfactorily performed.

Since the surface of the distal end of the insertion unit is protected against clouding. For example, the surface of the distal end of the insertion unit is coated with anti-clouding material. The other example is that the anti-clouding membrane which is integrally molded with the resin is disposed at the distal end of the insertion unit, the anti-clouding membrane is not peeled off from the distal end of the insertion unit, thereby preventing the distal ends of the illumination light transmitting optical fiber bundle and the image objectgive optical system from clouding. As a result, a stable image can be obtained.

The distal end of the image transmitting optical fiber bundle is integrally bonded by a resin at the distal end of the insertion unit through a pipe in which a lens is integrally concentrically molded by a resin. Therefore, the endoscope can be produced at a lower cost than a prior art endoscope having an objective optical system in which a pipe and a lens are separated from each other at the distal end of an image transmitting optical fiber bundle.

Since the wire is made of a resin, for example, aramid fiber and polyester resin, furthermore, the endoscope can be produced at a lower cost than a prior art endoscope which uses a wire rope configured by metal thin wires.

What is claimed is:

1. An endoscope comprising:
    means for inserting said endoscope in a human patient, said insertion means having a distal end, said insertion means comprising:
        a resin tube;
        an illumination light transmitting optical fiber bundle having a distal end, for guiding illumination light to said distal end of said insertion means;
        an image transmitting optical fiber bundle having a proximal end and a distal end, through which an image of an object illuminated with said illumination light is transmitted to said proximal end of said image transmitting optical fiber bundle;
    means for operating said endoscope, said operation means comprising:
        a light source for illuminating the object to be viewed through said image transmitting optical fiber bundle;
        a power source for supplying power to said light source;
        an eyepiece for observing the image of the object which is guided through said image transmitting optical fiber bundle;
        wherein one of a sheet with anti-clouding treatment and a layer with anti-clouding treatment is disposed on a surface of said distal end of said insertion means to thereby protect said surface against clouding.

2. An endoscope comprising:
    means for inserting said endoscope into a human patient, said insertion means having a distal end, said insertion means comprising:
        a connecting portion having a connecting surface; and
        a resin tube, having a bendable portion, said resin tube comprising:
            an illumination light transmitting optical fiber bundle for guiding illumination light to said distal end of said insertion means;
            an image transmitting optical fiber bundle through which an image of an object illuminated with said illumination light is transmitted to the connecting surface of said insertion means;
        a wire for bending said bendable portion;
    means for operating said endoscope, said operation means comprising:

a light source for illuminating the object to be viewed through said image transmitting optical fiber bundle;

a power source for supplying power to said light source;

an eyepiece for observing the image of the object which is guided through said image transmitting optical fiber bundle; and a wire operating mechanism which produces and relaxes tension in said wire; and means for detachable coupling said insertion means with said operation means;

wherein said wire incorporated in said insertion means is guided to adjacent a proximal end portion, and coupled with said wire operating mechanism disposed in said operation means; and wherein said wire operating mechanism includes a hook having an engaging portion, and a catch which slides in a direction of a center axis of said operation means, and which receives said engaging portion of said hook, said wire being coupled with said hook, and said hook being detachably connected to said catch by an engaging connection.

3. An endoscope comprising:

means for inserting said endoscope into a human patient, said insertion means having a distal end, said insertion means comprising:

a connecting portion having a connecting surface; and a resin tube, having a bendable portion, said resin tube comprising:

an illumination light transmitting optical fiber bundle for guiding illumination light to said distal end of said insertion means;

an image transmitting optical fiber bundle through which an image of an object illuminated with said illumination light is transmitted to the connecting surface of said insertion means;

a wire for bending said bendable portion; means for operating said endoscope, said operations means comprising:

a light source for illuminating the object to be viewed through said image transmitting optical fiber bundle;

a power source for supplying power to said light source;

an eyepiece for observing the image of the object which is guided through said image transmitting optical fiber bundle; and a wire operating mechanism which produces and relaxes tension in said wire; and means for detachably coupling said insertion means with said operation means; and one of a sheet with anti-clouding treatment and a layer with anti-clouding treatment disposed on a surface of said distal end of said insertion means to thereby protect said surface against clouding.

4. An endoscope comprising:

means for inserting said endoscope into a human patient, said insertion means having a distal end, said insertion means comprising:

a connecting portion having a connecting surface; and a resin tube, having a bendable portion, said resin tube comprising:

an illumination light transmitting optical fiber bundle for guiding illumination light to said distal end of said insertion means;

an image transmitting optical fiber bundle through which an image of an object illuminated with said illumination light is transmitted to the connecting surface of said insertion means;

a wire for bending said bendable portion; means for operating said endoscope, said operations means comprising:

a light source for illuminating the object to be viewed through said image transmitting optical fiber bundle;

a power source for supplying power to said light source;

an eyepiece for observing the image of the object which is guided through said image transmitting optical fiber bundle; and a wire operating mechanism which produces and relaxes tension in said wire; and means for detachably coupling said insertion means with said operation means; and a pipe, said pipe containing a lens integrally concentrically molded with said pipe by a resin;

wherein a distal end of said image transmitting optical fiber bundle is integrally bonded by a resin at said distal end of said insertion means through said pipe; and an anti-clouding material disposed on a surface of said distal end of said insertion means to thereby protect said surface against clouding.

5. An endoscope comprising:

means for inserting said endoscope into a human patient, said insertion means having a distal end, said insertion means comprising:

a connecting portion having a connecting surface; and a resin tube, having a bendable portion, said resin tube comprising:

an illumination light transmitting optical fiber bundle for guiding illumination light to said distal end of said insertion means;

an image transmitting optical fiber bundle through which an image of an object illuminated with said illumination light is transmitted to the connecting surface of said insertion means;

a wire for bending said bendable portion;

means for operating said endoscope, said operations means comprising:

a light source for illuminating the object to be viewed through said image transmitting optical fiber bundle;

a power source for supplying power to said light source;

an eyepiece for observing the image of the object which is guided through said image transmitting optical fiber bundle; and a wire operating mechanism which produces and relaxes tension in said wire; and means for detachably coupling said insertion means with said operation means; and an anti-clouding material which is integrally molded with a resin at said distal end of said insertion means.

6. An endoscope comprising:

means for inserting said endoscope into a human patient, said insertion means having a distal end, said insertion means comprising:

a resin tube;

an illumination light transmitting optical fiber bundle having a distal end, for guiding illumination light to said distal end of said insertion means;

an image transmitting optical fiber bundle having a proximal end and a distal end, through which an image of an object illuminated with said illumination light is transmitted to said proximal end of said image transmitting optical fiber bundle;

means for operating said endoscope, said operation means comprising:
- a light source for illuminating the object to be viewed through said image transmitting optical fiber bundle;
- a power source for supplying power to said light source;
- an eyepiece for observing the image of the object which is guided through said image transmitting optical fiber bundle; and
- wherein at least one of said distal end of said illumination light transmitting optical fiber bundle and said distal end of said image transmitting optical fiber bundle is integrally bonded together by a resin, with said distal end of said insertion means;
- wherein an anti-clouding material is integrally molded with said resin at said distal end of said insertion means.

7. An endoscope comprising:

means for inserting said endoscope into a human patient, said insertion means having a distal end, said insertion means comprising:
- a resin tube;
- an illumination light transmitting optical fiber bundle having a distal end, for guiding illumination light to said distal end of said insertion means;
- an image transmitting optical fiber bundle having a proximal end and a distal end, through which an image of an object illuminated with said illumination light is transmitted to said proximal end of said image transmitting optical fiber bundle;

means for operating said endoscope, said operation means comprising:
- a light source for illuminating the object to be viewed through said image transmitting optical fiber bundle;
- a power source for supplying power to said light source;
- an eyepiece for observing the image of the object which is guided through said image transmitting optical fiber bundle; and
- wherein said distal end of said insertion means includes a pipe, said pipe containing a lens integrally concentrically molded with said pipe by a resin, said distal end of said image transmitting fiber bundle being integrally bonded by a resin at said distal end of said insertion means through said pipe;
- wherein an anti-clouding material is disposed on a surface of said distal end of said insertion means to thereby protect said surface against clouding.

8. An endoscope comprising:

means for inserting said endoscope into a human patient, said insertion means having a distal end) said insertion means comprising:
- a connecting portion having a connecting surface; and
- a resin tube, having a bendable portion, said resin tube comprising:
  - an illumination light transmitting optical fiber bundle for guiding illumination light to said distal end of said insertion means;
  - an image transmitting optical fiber bundle through which an image of an object illuminated with said illumination light is transmitted to the connecting surface of said insertion means;
- a wire for bending said bendable portion;

means for operating said endoscope, said operation means comprising:
- a light source, for illuminating the object to be viewed through said image transmitting optical fiber bundle;
- a power source for supplying power to said light source;
- an eyepiece for observing the image of the object which is guided through said image transmitting optical fiber bundle; and
- a wire operating mechanism which produces and relaxes tension in said wire;
- means for detachably coupling said insertion means with said operation means; and
- wherein said wire incorporated in said insertion means is guided to adjacent a proximal end portion, and coupled with said wire operating mechanism disposed in said operation means;
- wherein said wire is guided to an outside of said adjacent proximal end portion of said connecting portion, and coupled with said wire operating mechanism at an external surface portion of said operation means; and
- wherein said wire operating mechanism includes a hook having an engaging portion, and a catch which slides in a direction of a center axis of said operation means, and which receives said engaging portion of said hook, said wire being coupled with said hook, and said hook being detachably connected to said catch by an engaging connection.

9. An endoscope comprising:

means for inserting said endoscope into a human patient, said insertion means having a distal end, said insertion means comprising:
- a connecting portion having a connecting surface; and
- a resin tube, having a bendable portion, said resin tube comprising:
  - an illumination light transmitting optical fiber bundle for guiding illumination light to said distal end of said insertion means;
  - an image transmitting optical fiber bundle through which an image of an object illuminated with said illumination light is transmitted to the connecting surface of said insertion means;
- wire for bending said bendable portion;

means for operating said endoscope, said operation means comprising:
- a light source for illuminating the object to be viewed through said image transmitting optical fiber bundle;
- a power source for supplying power to said light source;
- an eyepiece for observing the image of the object which is guided through said image transmitting optical fiber bundle;
- a wire operating mechanism which produces and relaxes tension in said wire; and
- means for detachably coupling said insertion means with said operation means;
- wherein said wire incorporated in said insertion means is guided to adjacent a proximal end portion, and coupled with said wire operating mechanism disposed in said operation means;
- wherein said wire operating mechanism includes a hook having an engaging portion, and a catch which slides in a direction of a center axis of said operation means, and which receives said engaging portion of said hook, said wire being coupled with said hook, and said hook being detachably connected to said catch by an engaging connection; and wherein at least two of a distal end of said illumination light transmitting optical fiber bundle, a distal end to said image transmitting optical fiber bundle, and a distal end of said wire are integrally bonded together by a resin at a distal end of said insertion means.

10. An endoscope comprising:

means for inserting said endoscope into a human patient, said insertion means having a distal end, said insertion means comprising:

a connecting portion having a connecting surface; and a resin tube, having a bendable portion, said resin tube comprising:

an illumination light transmitting optical fiber bundle for guiding illumination light to said distal end of said insertion means;

an image transmitting optical fiber bundle through which an image of an object illuminated with said illumination light is transmitted to the connecting surface of said insertion means;

a wire for bending said bendable portion;

means for operating said endoscope, said operation means comprising:

a light source for illuminating the object to be viewed through said image transmitting optical fiber bundle;

a power source for supplying power to said light source;

an eyepiece for observing the image of the object which is guided through said image transmitting optical fiber bundle;

a wire operating mechanism which produces and relaxes tension in said wire;

means for detachably coupling said insertion means with said operation means; and a pipe containing lens integrally concentrically molded with said pipe by a resin;

wherein said wire incorporated in said insertion means is guided to adjacent a proximal end portion, and coupled with said wire operating mechanism disposed in said operation means;

wherein said wire operating mechanism includes a hook having an engaging portion, and a catch which slides in a direction of a center axis of said operation means, and which receives said engaging portion of said hook, said wire being coupled with said hook, and said hook being detachably connected to said catch by an engaging connection; and wherein a distal end of said image transmitting optical fiber bundle is integrally bonded by said resin at said distal end of said insertion means through said pipe.

11. An endoscope comprising:

means for inserting said endoscope into a human patient, said insertion means having a distal end, said insertion means comprising:

a connecting portion having a connecting surface; and a resin tube, having a bendable portion, said resin tube comprising:

an illumination light transmitting optical fiber bundle for guiding illumination light to said distal end of said insertion means;

an image transmitting optical fiber bundle through which an image of an object illuminated with said illumination light is transmitted to the connecting surface of said insertion means;

a wire for bending said bendable portion; means for operating said endoscope, said operation means comprising:

a light source for illuminating the object to be viewed through said image transmitting optical fiber bundle;

a power source for supplying power to said light source;

an eyepiece for observing the image of the object which is guided through said image transmitting optical fiber bundle;

a wire operating mechanism which produces and relaxes tension in said wire; and means for detachably coupling said insertion means with said operation means;

wherein said wire incorporated in said insertion means is guided to adjacent a proximal end portion, and coupled with said wire operating mechanism disposed in said operation means;

wherein said wire operating mechanism includes a hook having an engaging portion, and a catch which slides in a direction of a center axis of said operation means, and which receives said engaging portion of said hook, said wire being coupled with said hook, and said hook being detachably connected to said catch by an engaging connection; and wherein said wire is made of a material selected from the group consisting of aramid fiber and polyester resin.

\* \* \* \* \*

UNITED STATES PATENT AND TRADEMARK OFFICE
CERTIFICATE OF CORRECTION

PATENT NO. : 6,004,263
DATED : December 21, 1999
INVENTOR(S) : Katsumi Nakaichi, et al.

It is certified that error appears in the above-identified patent and that said Letters Patent is hereby corrected as shown below:

On the title page:

The Assignee should read "<u>N</u>IHON KOHDEN CORPORATION", not "<u>H</u>IHON".

Signed and Sealed this

Eighth Day of May, 2001

*Attest:*

NICHOLAS P. GODICI

*Attesting Officer*     *Acting Director of the United States Patent and Trademark Office*